United States Patent [19]
Kameyama et al.

[11] Patent Number: 5,859,357
[45] Date of Patent: Jan. 12, 1999

[54] APPARATUS FOR MEASURING FRICTION FORCE BETWEEN A MAGNETIC HEAD AND A MAGNETIC DISK

[75] Inventors: Masaki Kameyama; Seigo Igaki, both of Kawasaki, Japan

[73] Assignee: Fujitsu Limited, Kawasaki, Japan

[21] Appl. No.: 771,200

[22] Filed: Dec. 20, 1996

[30] Foreign Application Priority Data

Dec. 25, 1995 [JP] Japan .................................. 7-337132

[51] Int. Cl.⁶ ...................................................... G01N 3/56
[52] U.S. Cl. ...................................................... 73/9; 73/7
[58] Field of Search ................................................ 73/7, 9

[56] References Cited

U.S. PATENT DOCUMENTS

| | | | |
|---|---|---|---|
| 4,646,557 | 3/1987 | Park | 73/9 |
| 5,115,664 | 5/1992 | Hegde et al. | 73/9 |
| 5,212,657 | 5/1993 | Uchikawa et al. | 73/9 |
| 5,539,592 | 7/1996 | Banks et al. | 73/9 |

FOREIGN PATENT DOCUMENTS

| | | |
|---|---|---|
| 52-153406 | 12/1977 | Japan . |
| 61-215946 | 9/1986 | Japan . |
| 63-11825 | 1/1988 | Japan . |
| 63-48607 | 3/1988 | Japan . |
| 63-52037 | 3/1988 | Japan . |
| 63-52038 | 3/1988 | Japan . |
| 3238342 | 10/1991 | Japan . |
| 6138019 | 5/1994 | Japan . |
| 7270305 | 10/1995 | Japan . |
| 87511 | 1/1996 | Japan . |

*Primary Examiner*—Max H. Noori
*Attorney, Agent, or Firm*—Greer, Burns, & Crain, Ltd.

[57] ABSTRACT

An apparatus for measuring a maximum static friction force is disclosed, in which the displacement of the relative positions of first and second objects due to the operation of a driving unit is suppressed for measuring an accurate static friction force characteristic. The static friction force measuring apparatus for measuring the static friction characteristic between a first object fixed on a mounting base and a second object in contact with the first object and held in a holder comprises an external force buffer interposed between the mounting base and the mounting base side fixed end of the apparatus, a speed controller arranged in the drive unit for controlling the relative speeds of the holder and the mounting base to a level sufficiently low as compared with the resonance frequency of a frictional force detector, and a device for suppressing the displacement of the relative positions of the first and second objects to such an extent that the external force exerted substantially in parallel with the contact surface between the two objects exceeds the maximum static friction force. The frictional force detector detects the maximum static friction force immediately before the displacement begins between the two objects.

12 Claims, 17 Drawing Sheets

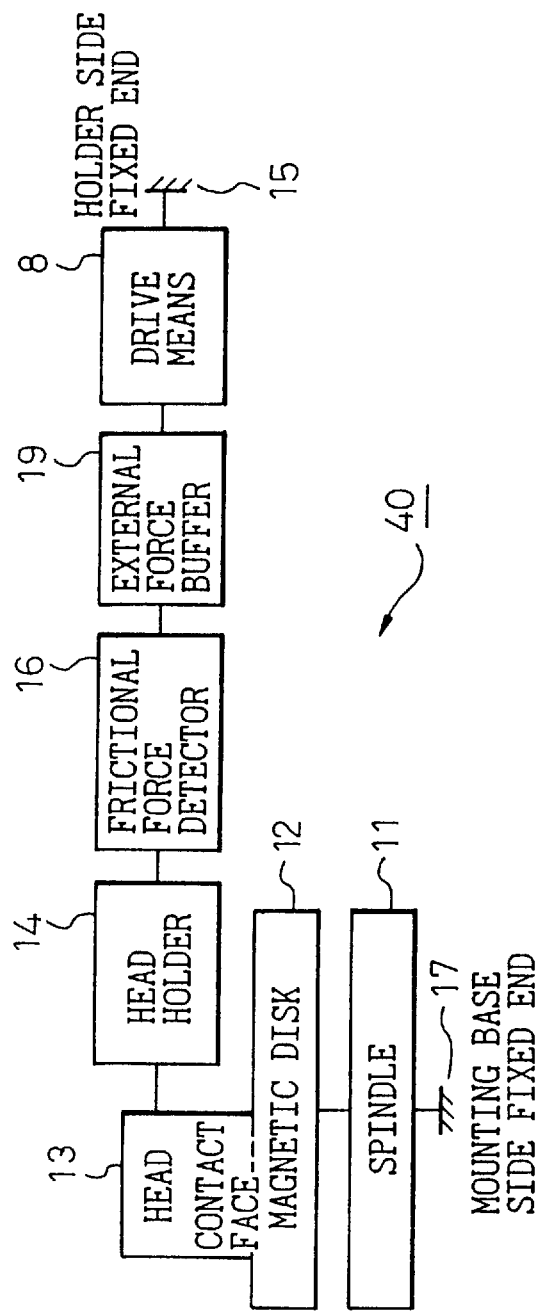

Fig.12

(NOTE: FIGURE IN THE PARENTHESIS IS THE PERCENTAGE WHEN TURNING BY HAND IS 100) (n=10)

| DRIVING MEANS | | TURNING BY HAND | FALSE LOW ACCELERATION MOTOR | MOTOR OF TESTING MACHINE | MOTOR OF TESTING MACHINE |
|---|---|---|---|---|---|
| SENSOR | | μ SENSOR | μ SENSOR (LOAD CELL) | μ SENSOR | LOAD CELL |
| SAMPLE A | AVERAGE VALUE | 5.59 (100) | 5.80 (104) | 6.88 (123) | 1.22 (22) |
| | MAXIMUM VALUE | 6.02 | 6.50 | 8.86 | 1.28 |
| | MINIMUM VALUE | 5.16 | 5.76 | 5.02 | 1.11 |
| SAMPLE B | AVERAGE VALUE | 0.50 (100) | 0.50 (100) | 0.67 (134) | 0.41 (82) |
| | MAXIMUM VALUE | 0.53 | 0.53 | 0.76 | 0.43 |
| | MINIMUM VALUE | 0.46 | 0.47 | 0.56 | 0.37 |
| SAMPLE C | AVERAGE VALUE | 7.54 (100) | 8.11 (108) | 9.39 (125) | 2.03 (27) |
| | MAXIMUM VALUE | 10.63 | 10.19 | 13.12 | 2.50 |
| | MINIMUM VALUE | 5.42 | 5.64 | 7.63 | 1.88 |

APPARATUS FOR MEASURING FRICTION FORCE BETWEEN A MAGNETIC HEAD AND A MAGNETIC DISK

BACKGROUND OF THE INVENTION

1. Field of the Invention

The present invention relates to an apparatus for measuring static friction force and, in particular, to an apparatus for measuring the static friction force between a magnetic disk and a magnetic head of a hard disk unit.

2. Description of the Related Art

In recent years, the requirement for increasing the storage capacity of the hard disk units has made it necessary to increase the density of magnetic disks. The current trend, therefore, is toward decreasing the flying height of the magnetic head above the magnetic disk. Specifically, in the case where an increased recording density of a magnetic disk is desired for the hard disk unit, the magnetic disk and the magnetic head are required to operate in positions closer to each other by reducing the spacing therebetween. For a stable air-bearing characteristic of the magnetic head to be maintained with a decreased flying height of the magnetic head from the magnetic disk, a smooth surface of the magnetic disk is required. Once the surface of the magnetic disk is smooth, however, the magnetic disk in a stationary state and the magnetic head attract each other. This poses the problem of a larger torque required for restarting the hard disk unit.

In order to obviate this problem, vigorous tribology research and development efforts are continuing to solve the two conflicting objects of smoothing the surface of the magnetic disk on the one hand and preventing the attraction of the magnetic head to the surface of the magnetic disk in stationary state on the other. The demand is very high, therefore, for an apparatus capable of measuring the static friction force between the magnetic head and the magnetic disk with high accuracy.

In a conventional apparatus for measuring the static friction force between magnetic disk and magnetic head, the magnetic disk is fixed on a mounting base movable by motor having an end thereof secured to a mounting base side fixed end of the apparatus. The magnetic head placed in contact on the magnetic disk, on the other hand, is held by a holder connected to a friction force detector having an end thereof secured to a holder side fixed end of the apparatus.

In the case where the static friction force is measured using a static friction force measuring apparatus configured as described above, a motor is activated to generate an external force and thus to move the mounting base. Then, the maximum output value of the friction detector is detected to calculate the static coefficient of friction is. Specifically, with the head kept in close contact with the magnetic disk under the spring load of the head, the motor is driven at low speed. The maximum output value produced from the friction force detector after starting the motor is determined as a maximum static friction force.

In this conventional static friction force measuring method described above, however, the static friction force between the magnetic disk and the magnetic head cannot be measured accurately, in view of the fact that the true friction force between the magnetic disk and the magnetic head undergoes changes too rapid to be followed by the response characteristic of the friction force detector.

In a method conceived to improve this point, a wide-band sensor high in response speed (about 5 kHz) comprising a combination of a parallel spring and a distortion gage is used as a friction detector. The use of a wide-band sensor as a friction force detector, however, undesirably causes the resonance of the wide-band sensor under the effect of acceleration at the time of starting the motor, thereby making it impossible to determine a true friction force.

SUMMARY OF THE INVENTION

The object of the present invention is to provide a static friction force measuring apparatus for measuring the static friction characteristic between a first object fixed on a mounting base with an end thereof connected to a fixed end of the apparatus and a second object in contact with the first object and having an end thereof held by a holder connected to the other fixed end of the apparatus, comprising a friction detector interposed at an arbitrary position except for a friction force generating section between the two fixed ends, driving means for applying an external force exerted substantially in parallel directions to the contact surfaces of the first and the second objects, and means for alleviating the external force exerted on the static friction force measuring apparatus and thereby suppressing the displacement of the relative positions of the first object and the second object which otherwise would be caused by the operation of the driving means, thereby making it possible to measure the static friction force characteristic of the contact surface between the first object and the second object without being affected by the external force.

According to one aspect of the invention, there is provided a static friction force measuring apparatus for applying a force in a direction substantially parallel with the contact surface between a magnetic head and a magnetic disk and measuring the maximum static friction force immediately before the displacement of the relative positions of the magnetic head and the magnetic disk, comprising means acting as a buffer for alleviating the external force exerted between the head side fixed end of the apparatus and the mounting base side fixed end of the apparatus and suppressing the displacement of the relative positions of the magnetic head and the magnetic disk which might otherwise be caused by the operation of driving means. It is thus possible to measure the characteristic of the static friction force between the magnetic head and the magnetic disk in a state free of displacement of the relative positions of the magnetic head and the magnetic disk even under an external force which may be exerted between the head and the magnetic disk.

According to another aspect of the invention, there is provided a static friction force measuring apparatus for applying a force in a direction substantially parallel with the contact surface between a first object and a second object and measuring the maximum static friction force immediately before displacement of the relative positions of the first and second objects, comprising means acting as a buffer for alleviating the external force exerted between the fixed end on the first object side of the apparatus and the fixed end on the second object side of the apparatus and thereby suppressing the displacement of the relative positions of the first object and the second object which otherwise might be caused under the operation of driving means. It is thus possible to measure the characteristic of the static friction force between the first and second objects in a state free of the displacement of the relative positions of the first and second object under an external force imposed from the driving means.

BRIEF DESCRIPTION OF THE DRAWINGS

The present invention will be more clearly understood from the description as set forth below with reference to the accompanying drawings, wherein:

FIG. 10A is a block diagram showing a configuration of a static friction force measuring apparatus according to a fourth embodiment of the invention.

FIG. 12 is a table showing the effects of a static friction force measuring apparatus according to the invention.

DESCRIPTION OF THE PREFERRED EMBODIMENTS

Before describing the preferred embodiments, an explanation will be given of the conventional apparatus for measuring static friction force shown in FIGS. 1A to 3.

Figure 1A:
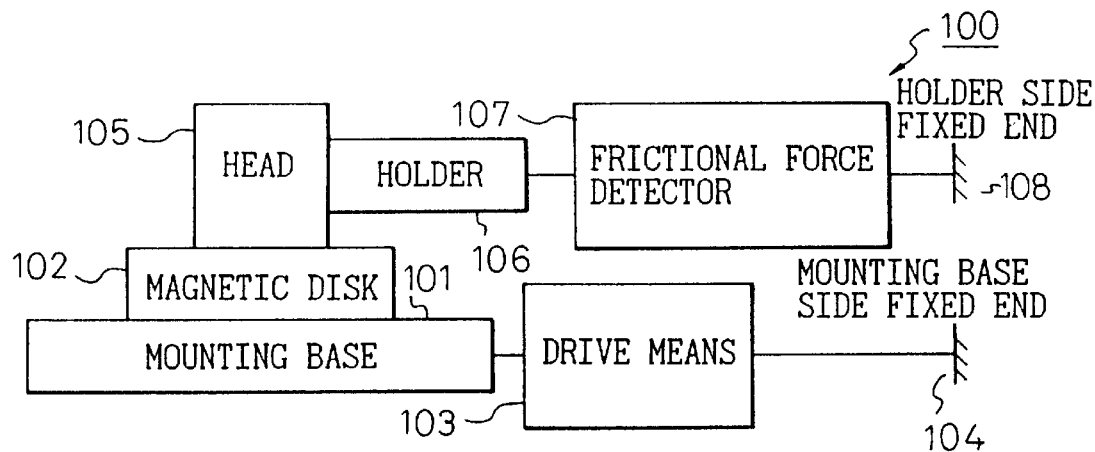
FIG. 1A is a block diagram showing a configuration of a conventional static friction force measuring apparatus.

FIG. 1A shows a configuration of a conventional static friction force measuring apparatus 100 for measuring the static friction force between a magnetic disk and a magnetic head. A magnetic disk 102 is fixed on a mounting base 101 which is movable by drive means 103. The drive means 103 is a motor, for example. An end of the drive means 103 is secured to a mounting base side fixed end 104 of the apparatus. A head 105 arranged on the magnetic disk 102, on the other hand, is held in a holder 106, which is connected to a frictional force detector 107. An end of the frictional force detector 107 is fixed on a holder side fixed end 108 of the apparatus.

Figure 1B:
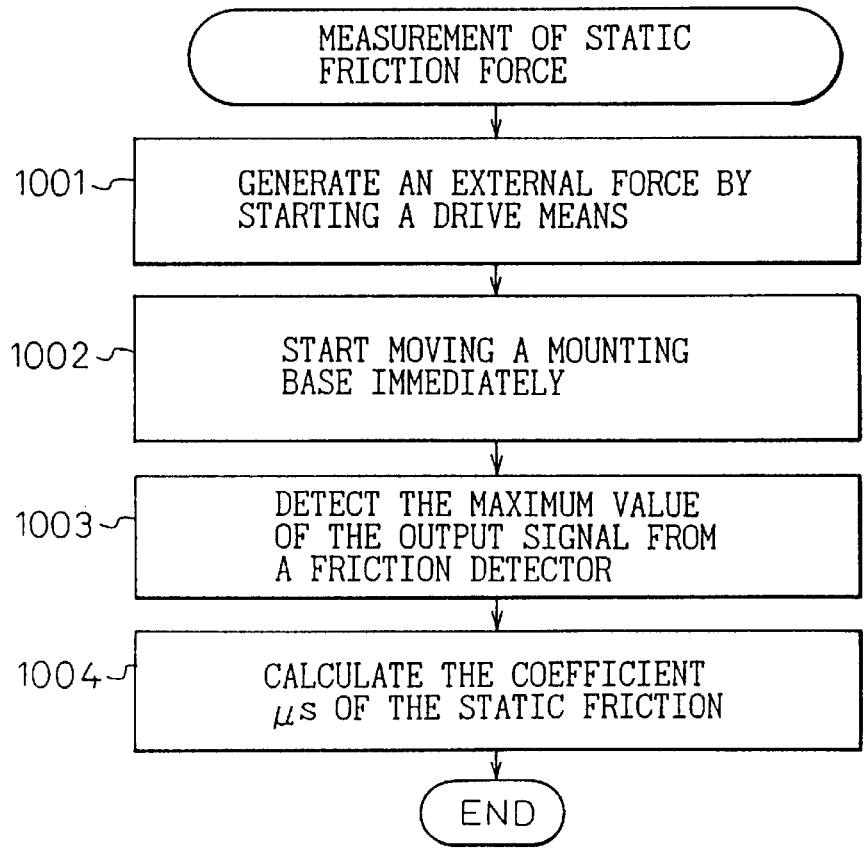
FIG. 1B is a flowchart showing the steps of measuring the static friction force by the static friction force measuring apparatus shown in FIG. 1A.

In the case where the static friction force is measured using the static friction force measuring apparatus 100 having the above-mentioned configuration, the measuring steps shown in FIG. 1B are followed. Specifically, step 1001 generates an external force by actuating drive means 103, and step 1002 immediately starts the movement of the mounting base 101. Step 1003 detects the maximum value of the output of the friction force detector 107, and step 1004 calculates the static friction coefficient $\mu$s. More specifically, with the head 105 kept in close contact with the magnetic disk 102 under the spring load of the head 105, the drive means 103 is driven at low speed, so that a maximum output value subsequently detected by the friction force detector 107 is used as a maximum static friction force.

The conventional method of measuring static friction force, however, poses the problem that the static friction force between the magnetic disk and the magnetic head cannot be accurately measured in the case where the recording density of the magnetic disk is high resulting in surface of the magnetic disk being smooth.

This problem will be described in detail below.

In the configuration of FIG. 1A, let F be the friction force between the magnetic disk 102 and the head 105, Fs the attractive force between them, and W the spring pressure applied by the holder 106 to the head 105. Then, the relation given below holds.

$$F=\mu(W+Fs)$$

As the surface of the magnetic disk 102 becomes smoother, the attractive force Fs increases, thereby often increasing the difference between static friction force and dynamic friction force. An explanation will be given of the problem attributable to the response speed of the sensor of the friction force detector 107 in such a case.

Figure 2A:
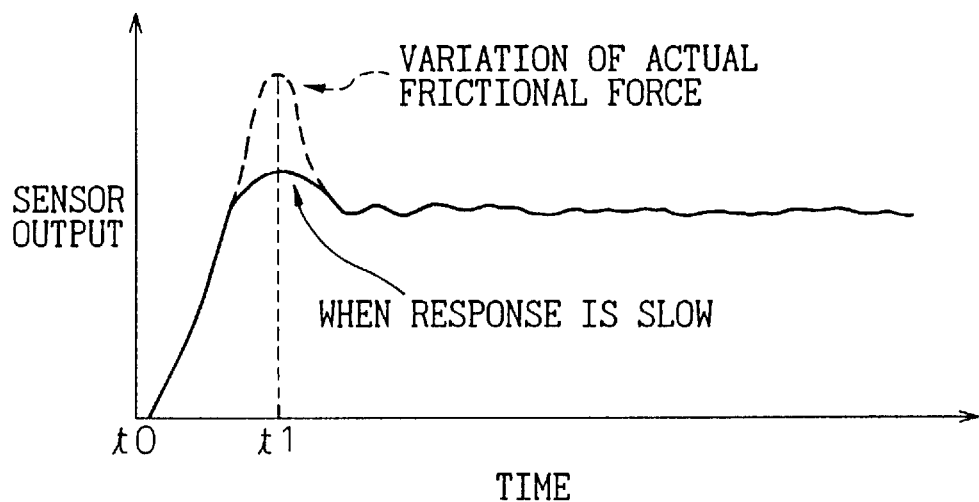
FIG. 2A is a characteristic diagram showing the effect of response speed of a friction force detector of the conventional static friction force measuring apparatus using a sensor having a low response speed.

In the static friction force measuring apparatus 100 shown in FIG. 1A, assume that the mounting base 101 is moved by use of the drive means 103 and that the change of the true friction force between the magnetic disk 102 and the head 105 is represented by the dashed characteristic curve in FIG. 2A. The portion of the characteristic shown in FIG. 2A from time t0 to t1 represents the change in static friction force between the magnetic disk 102 and the magnetic head 105, while the characteristic from time point t1 represents the change of dynamic friction force. In the case where a sensor of low response speed (about 50 Hz) such as a load cell is used with the friction force detector 107 with such a large difference between maximum static friction force and dynamic friction force as in the foregoing case, the output of the load cell becomes low as shown by solid line in FIG. 2A. Consequently, under the state where the difference is large between maximum static friction force and dynamic friction force, the conventional static friction force measuring apparatus encounters the problem that it cannot correctly detect the change in true friction force between the magnetic disk 102 and the head 105.

Figure 2B:
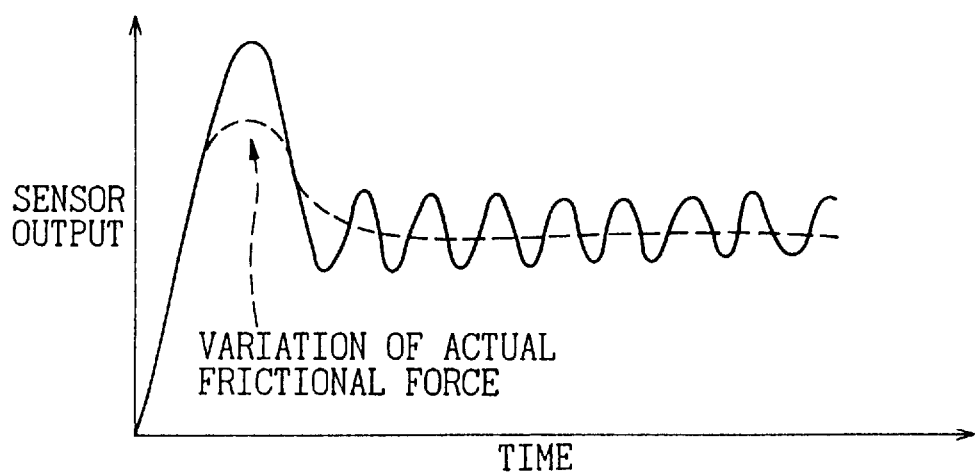
FIG. 2B is a characteristic diagram showing the effect of resonance of a friction force detector of the conventional static friction force measuring apparatus using a wide-band sensor.
Figure 3:
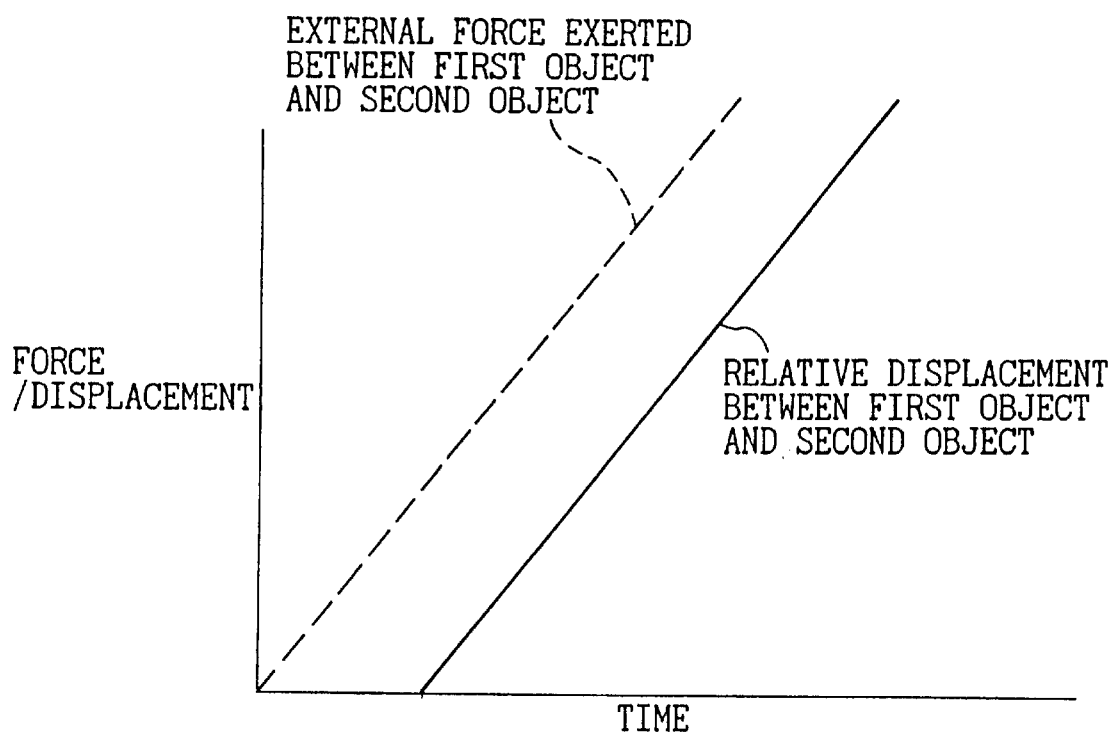
FIG. 3 is a characteristic diagram showing the characteristic of the change in relative positions of the magnetic head and the magnetic disk with time.

In an attempt to improve this point, a wide-band sensor with a high response speed (about 5 kHz) including a combination of a parallel spring and a distortion gage has been used as the frictional force detector 107. The use of a wide-band sensor as the frictional force detector 107, however, undesirably causes the wide-band sensor to resonate under the effect of acceleration at the time of starting the motor and gives a sensor output as shown by solid line in FIG. 2B. The dashed curve in FIG. 2B represents the change in true friction force between the magnetic disk 102 and the head 105. As a result, even the use of a wide-band sensor cannot obviate the problem that the true friction force cannot be detected correctly.

The present invention is intended to obviate these problem points of the conventional static friction force measuring apparatus. In a static friction force measuring apparatus according to the invention, a force is applied in a direction substantially parallel with the contact surface between a first object and a second object for measuring the maximum static friction force immediately before displacement of the relative positions of the first and second objects. The static friction force measuring apparatus according to this invention comprises buffer means for alleviating the external force between the fixed end of the apparatus near the side of the first object and the fixed end of the apparatus near the side of the second object and thereby suppressing the displacement of the relative positions of the first object and the second object which otherwise might be enhanced by the operation of the drive means. As shown by solid line in FIG. 3, the displacement of the relative positions of the first and second object is eliminated while being subjected to an external force applied as shown by dashed line, thereby making it possible to measure the static friction force between the first and second objects accurately by the static friction force measuring apparatus.

Figure 4A:
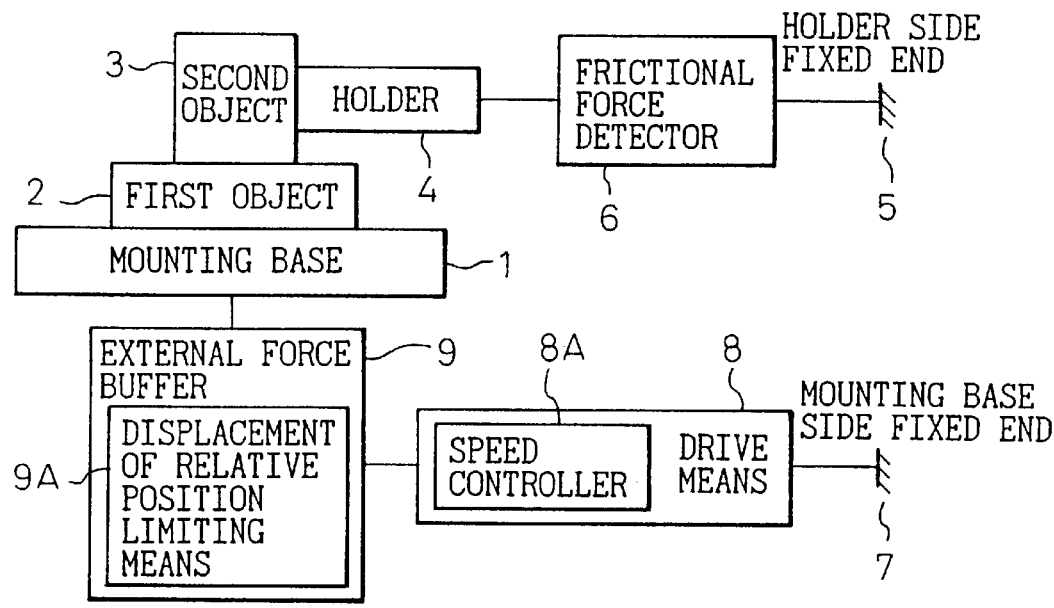
FIG. 4A is a block diagram showing a basic configuration of a static friction force measuring apparatus comprising driving means for driving a first object according to the invention.
Figure 4B:
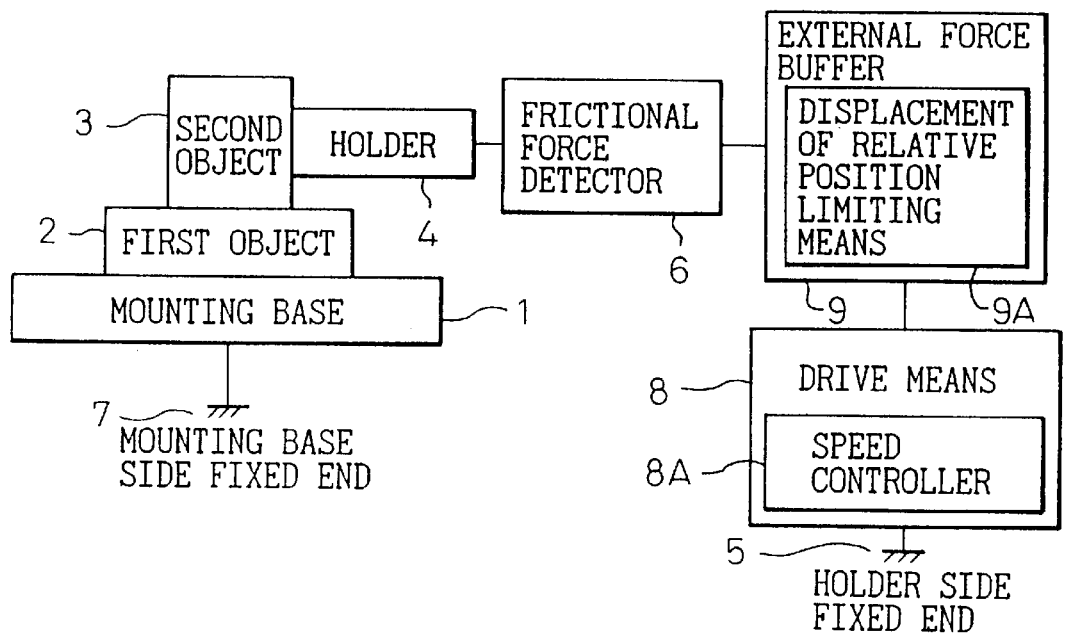
FIG. 4B is a block diagram showing a basic configuration of a static friction force measuring apparatus comprising driving means for driving a second object according to the invention.

FIGS. 4A and 4B show two aspects of the static friction force measuring apparatus according to the invention. The static friction force measuring apparatus according to the first aspect shown in FIG. 4A is for measuring the static friction characteristic between a first object 2 fixed on a mounting base 1 and a second object 3 in contact with the first object 2. In the static friction force measuring apparatus according to the first aspect, the second object 3 is held in a holder 4, which in turn is connected to a frictional force detector 6 secured to a fixed end 5 of the apparatus. The mounting base 1, on the other hand, is connected to an external force buffer 9 which is connected to a drive means 8 with an end thereof secured to a fixed end 7 of the apparatus.

The drive means 8 applies an external force in a direction substantially parallel with the contact surface between the objects 2 and 3, and has a speed controller 8A built therein for controlling the speed of relative movement between the holder 4 and the mounting base 1 to a sufficiently low level as compared with the resonance frequency of the frictional force detector 6. The external force buffer 9 also includes relative position change suppressor 9A for suppressing the displacement of the relative positions of the objects 2 and 3 until the external force exerted in a direction substantially parallel with the contact surface between the objects 2 and 3 exceeds the maximum static friction force. With this configuration, the maximum static friction force immediately before the displacement of the objects 2 and 3 starts is measured by the frictional force detector 6.

A static friction force measuring apparatus according to a second aspect of the invention shown in FIG. 4B is used for measuring the static friction characteristic between a first object 2 fixed on a mounting base 1 and a second object 3 placed on the first object 2. In the static friction force measuring apparatus according to the second aspect of the invention, the first object 2 is fixed on the mounting base 1 and the second object 3 placed on the first object 2 is held in the holder 4 connected to the frictional force detector 6 in a similar manner to the static friction force measuring apparatus according to the first aspect.

The static friction force measuring apparatus according to the second aspect differs from the static friction force measuring apparatus according to the first aspect with respect to the relative positioning of the external force buffer 9 and the frictional force detector 6. Notably, the static friction force measuring apparatus according to the second aspect, the mounting base 1 is secured directly on the fixed end 7 of the apparatus and the frictional force detector 6 is connected to the external force buffer 9, which in turn is connected to the drive means 8 with an end thereof secured to the fixed end 5.

The drive means 8 exerts an external force in a direction substantially parallel with the contact surface between the objects 2 and 3. The drive means 8 has built therein a speed controller 8A for controlling the relative speed of movement between the holder 4 and the mounting base 1 to a sufficiently low level as compared with the resonance frequency of the frictional force detector 6. Also, the drive means 8 includes a relative position displacement suppressor 9A for suppressing the displacement of the relative positions of the objects 2 and 3 until the external force exerted in a direction substantially parallel with the contact surface between the objects 2 and 3 arranged on the external force buffer 9 exceeds the maximum static friction force. With this configuration, the maximum static friction force immediately before the initiation of the displacement of the objects 2 and 3 can be measured by the frictional force detector 6.

Now, the two aspects of the static friction force measuring apparatus according to the present invention described above with reference to FIGS. 4A and 4B will be specifically explained below with reference to a specific embodiment in which the first object is a magnetic disk and the second object is a magnetic head.

Figure 5A:
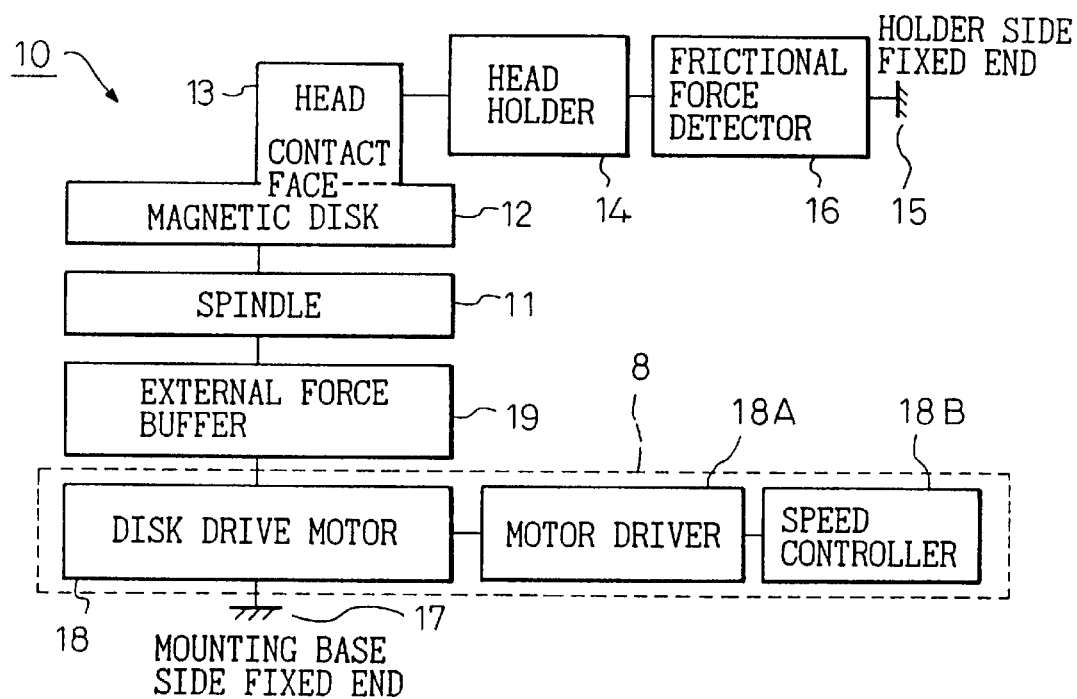
FIG. 5A is a block diagram showing a configuration of a static friction force measuring apparatus according to the first embodiment of the invention.

FIG. 5A is a block diagram showing a configuration of the static friction force measuring apparatus 10 according to the first embodiment of the invention for measuring the static friction force between a magnetic disk 12 and a head 13.

The magnetic disk 12 is fixed on a spindle 11 providing a mounting base. The rotative axis of the spindle 11 is coupled to the rotative axis of a disk drive motor 18 providing a drive means through an external buffer 19. The disk drive motor 18 is secured to a mounting base side fixed end 17 of the apparatus, and is connected to a motor driver 18A and a speed controller 18B.

The head 13, on the other hand, has an air-bearing surface thereof in contact with the upper surface of the magnetic disk 12, thereby constituting a contact surface. The head 13 is held in a head holder 14 which in turn is connected to a frictional force detector 16 with an end thereof secured to the holder side fixed end 15 of the apparatus.

Figure 5B:
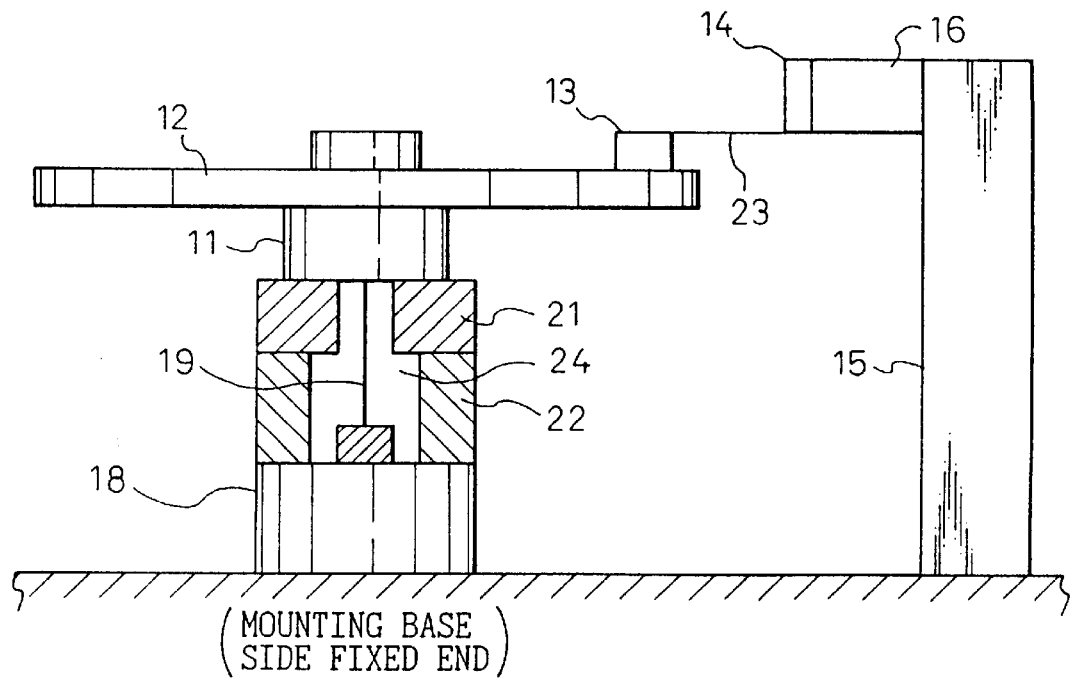
FIG. 5B is a partly cutaway side view showing a specific example of the static friction force measuring apparatus according to the invention.

FIG. 5B more specifically shows a configuration of the static friction force measuring apparatus 10 of FIG. 5A including the configuration of the external buffer 19 according to an embodiment. In FIG. 5B, those component parts identical to the corresponding ones in FIG. 5A are designated by the same reference numerals, respectively.

The head 13 is mounted on the head holder 14 through a gimbal spring 23, and a wide-band sensor (i sensor) is arranged adjacently to the head holder 14. The wide-band sensor 16 is fixed on a support 15 providing the holder side fixed end of the apparatus. Also, the spindle 11 carrying the magnetic disk 12 has a bearing 21 mounted thereon, so that the magnetic disk 12 mounted on the spindle 11 can rotate about the rotative axis of the spindle 11. A spacer 22 is interposed between the bearing 21 and the disk drive-motor 18. A torsion spring 19 is arranged in the space 24 formed by the spacer 22, and provides a relative position displacement suppressor of the external buffer for directly coupling the rotative axis of spindle 11 and that of the disk drive motor 18.

Figure 6:
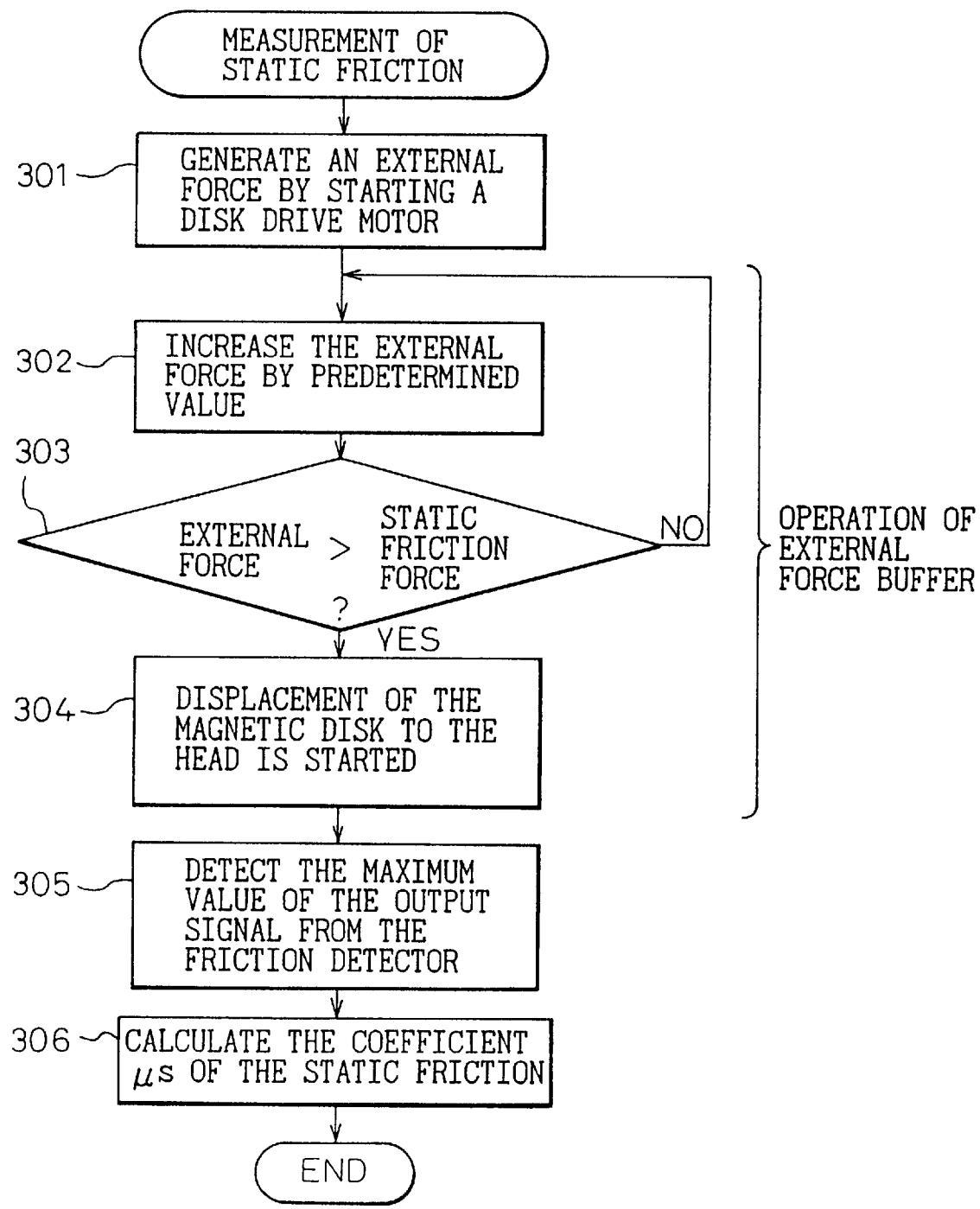
FIG. 6 is a flowchart showing the steps of measuring the static friction force by a static friction measuring apparatus according to the invention.

The steps of measuring the static friction force by the static friction force measuring apparatus 10 configured as described above will be explained with reference to the flowchart of FIG. 6.

In step 301, the disk drive motor 18 making up drive means is started to generate an external force. Step 302 increases the driving force of the disk drive motor 18 by a predetermined amount thereby to increase the external force by a predetermined amount. The next step 303 decides whether or not the external force generated by the disk drive motor 18 has exceeded the static friction force between the magnetic disk 12 and the head 13. In the case where the external force generated by the disk drive motor 18 has not exceeded the static friction force between the magnetic disk 12 and the head 13, the process returns to step 302 for increasing the driving force of the disk drive motor 18 again by a predetermined amount to thereby increase the external force by a predetermined amount.

In the case where the decision in step 303 is that the external force generated by the disk drive motor 18 has exceeded the static friction force between the magnetic disk 12 and the head 13, on the other hand, the process proceeds to step 304 for starting the displacement between the magnetic disk 12 and the head 13. Step 305 detects the maximum value of the output of the frictional force detector, and step 306 calculates the static friction coefficient $\mu s$.

Specifically, while the head 13 is kept in close contact with the magnetic disk 12 while being subjected to a spring load by means of the gimbal spring 23, the disk drive motor 18 is started slowly. Then, an external force in a direction substantially parallel with the contact surface between the magnetic disk 12 and the head 13 is exerted to progressively increase the external force and the friction force.

In this case, the above-mentioned conventional static friction force measuring apparatus 100 is such that the external force generated by the disk drive motor 18 is applied to the contact surface directly and therefore has posed the problem that the detection value of the friction force oscillates with generation of a large acceleration of the external force. With the static friction force measuring apparatus 10 according to this invention comprising a torsion spring 19 provided on the rotative axis of the disk drive motor 18 and the spindle 11, by contrast, the relative positions of the magnetic disk 12 and the head 13 are not displaced but only the torsion spring 19 is twisted and deformed before the external force generated by the disk drive motor 18 exceeds the friction force of the contact surface between the magnetic disk 12 and the head 13. At the instant when the external force generated by the disk drive motor 18 exceeds the friction force of the contact surface between the magnetic disk 12 and the head 13, the relative positions of the magnetic disk 12 and the head 13 are displaced for the first time. The maximum static friction force can thus be measured with high accuracy.

The external force generated by the disk drive motor 18 basically increases monotonically, although there may be an intermediate period when the external force remains constant or decreases. The rate at which the external force increases is required to be equivalent to about one half or less the resonance frequency of the wide-band sensor 16.

Figure 7A:
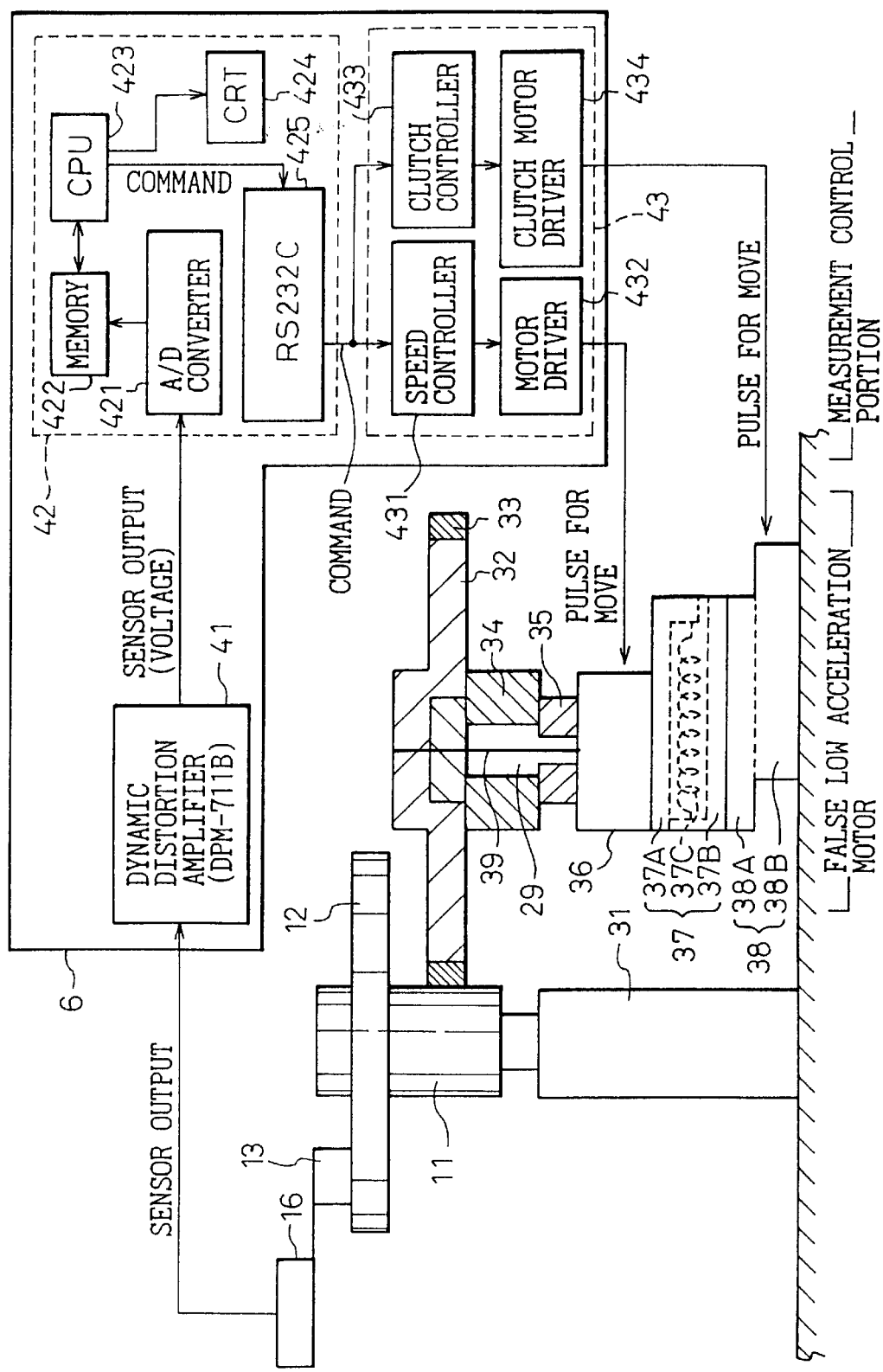
FIG. 7A is a diagram showing a configuration of another specific example of the static friction force measuring apparatus of FIG. 5A.

FIG. 7A shows a more specific configuration of the static friction force measuring apparatus of FIG. 5A, including a configuration of the external force buffer 19 according to another embodiment and a detailed configuration of an electrical circuit for measuring the static friction force between the magnetic disk 12 and the head 13. In FIG. 7A, those component parts identical to the corresponding component parts in FIG. 5A are designated by the same reference numerals, respectively.

According to this embodiment, the magnetic disk 12 is mounted on the spindle 11 which is rotatably held on a bearing base 31. The outer peripheral surface of the spindle 11 is in contact with a rubber ring 33 fitted on the outer peripheral surface of a roller 32 supported rotatably on a bearing 34. The bearing 34 is connected to a roller drive motor 36 through a spacer 35. A torsion spring 39 is arranged in a space 29 defined by the bearing 34 and the spacer 35. The torsion spring 39 functions as a relative position displacement suppressor for the external buffer directly coupling the rotative axis of the roller 32 and the rotative axis of the roller drive motor 36. The roller drive motor 36 is arranged on an X stage 37 which in turn is mounted on an X auto stage 38 and constitutes a false low-acceleration motor.

The wide-band sensor 16 is connected to the head 13 and detects the static friction force between the magnetic disk 12 and the head 13 as a voltage proportional to the force exerted on it. The output of the wide-band sensor 16 is applied to a frictional force detector 6. The frictional force detector 6 includes a dynamic distortion amplifier 41, a control circuit 42 and a stage controller 43. The output of the wide-band sensor 16 is applied to the dynamic distortion amplifier 41 where it is amplified and output. This output is applied to an A/D converter 421 of the control circuit 42 including a personal computer or the like, where it is converted into a digital signal. The control circuit 42 includes a memory 422, a CPU 423, a display unit (CRT) 424 and an RS232C interface 425. The memory 422 stores the friction force data in the form of digital signals converted by the A/D converter 421. The CPU 423 calculates the static friction force from the data stored in the memory 422. The static friction force thus calculated is displayed on the display unit (CRT) 424. Also, the RS232C interface 425 transmits the command sent from the CPU 423 to the stage controller 43.

In this way, the output of the wide-band sensor 16 is A/D converted in the friction force detector 6 and applied to the stage controller 43 as a command. The stage controller 43 includes a speed controller 431, a motor driver 432, a clutch controller 433 and a clutch motor driver 434. The stage controller 43 has the function of recognizing the command sent from the CPU 42 and driving the X stage 37 and the X auto stage 38. A microcomputer is also built in the stage controller 43.

The command sent from the CPU 42 is applied to the speed controller 431 and the clutch controller 433. The speed controller 431 recognizes the input command and applies a drive pulse generation signal to the motor driver 432. The drive pulse is output from the motor driver 432 for controlling the rotation of the roller driver motor 36. The clutch controller 433 recognizes the input command and applies a drive pulse generation signal to the clutch motor driver 434. The drive pulse is output from the clutch motor driver 434 for controlling the movement of the X stage 37 and the X auto stage 38. The X stage 37 and the X auto stage 38 have the function of pressing the roller 32 against the spindle 11 at a predetermined pressure.

The X stage 37 includes an upper stage 37A, a lower stage 37B and a spring 37C. The X auto stage 38, on the other hand, includes a movable stage 38A and a fixed stage 38B. The lower stage 37B is fixed on the movable stage 38A, while the upper stage 37A is movable with respect to the lower stage 37B. The X stage 37 and the X auto stage 38 are initially in the state shown in FIG. 7B.

Figure 7B:
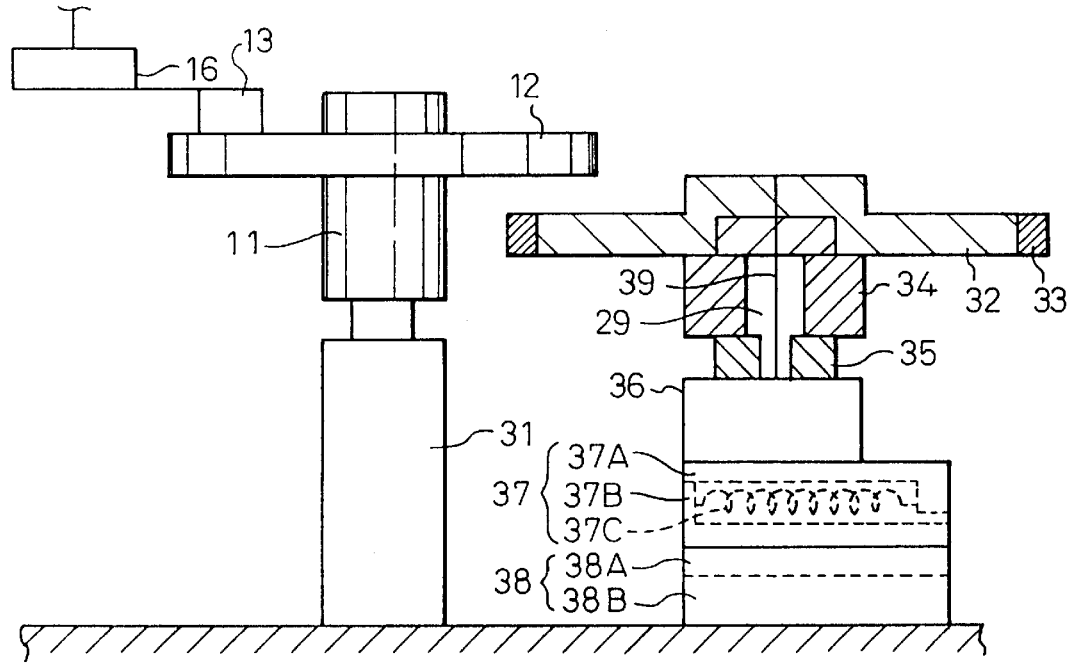
FIGS. 7B and 7C are diagrams for explaining the operation of an X stage and an X auto stage shown in FIG. 7A.
Figure 7C:
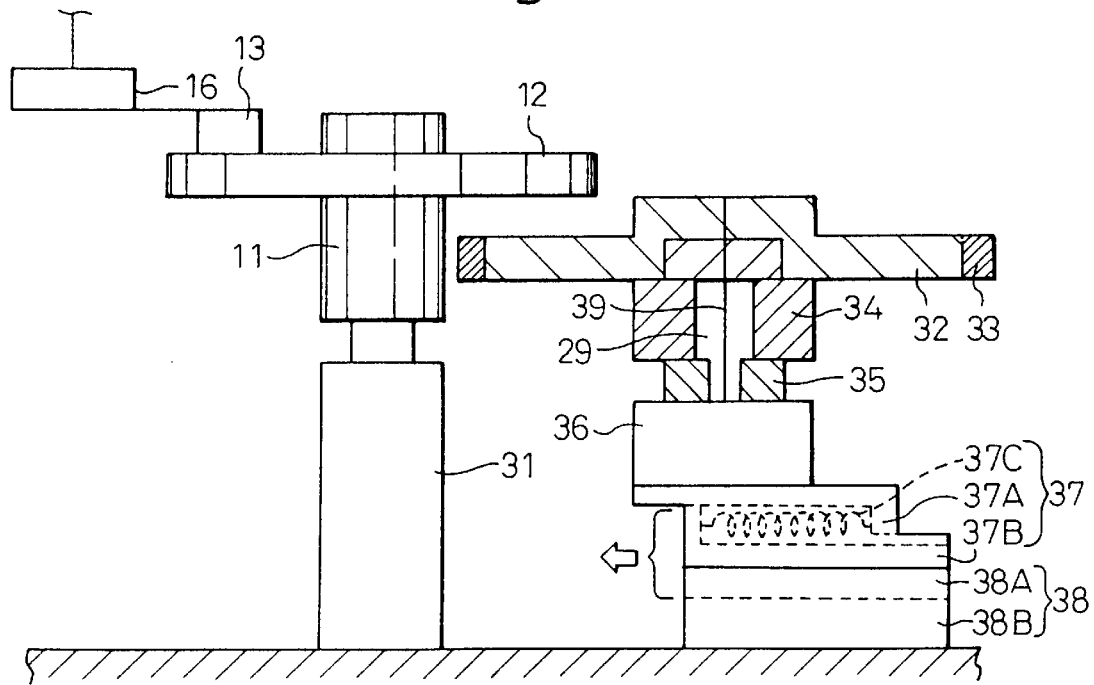

Under the condition of FIG. 7B, it is assumed that the micrometer head not shown is removed. The force of the spring 37C built in the X stage 37 causes one side of the stage 37A of the X stage 37 to jump out, as shown in FIG. 7C. Assuming that the X auto stage 38 moves toward the spindle 11 under this condition, the roller 32 comes into contact with the spindle 11. Upon further movement of the X auto stage 38 toward the spindle 11, the spring in the X stage 37 extends into the state shown in FIG. 7A. The pressure exerted by the roller 32 against the spindle 11 can be appropriately controlled by setting the amount by which the spring 37C is extended (the amount of movement of the X auto stage 38).

Figure 8A:
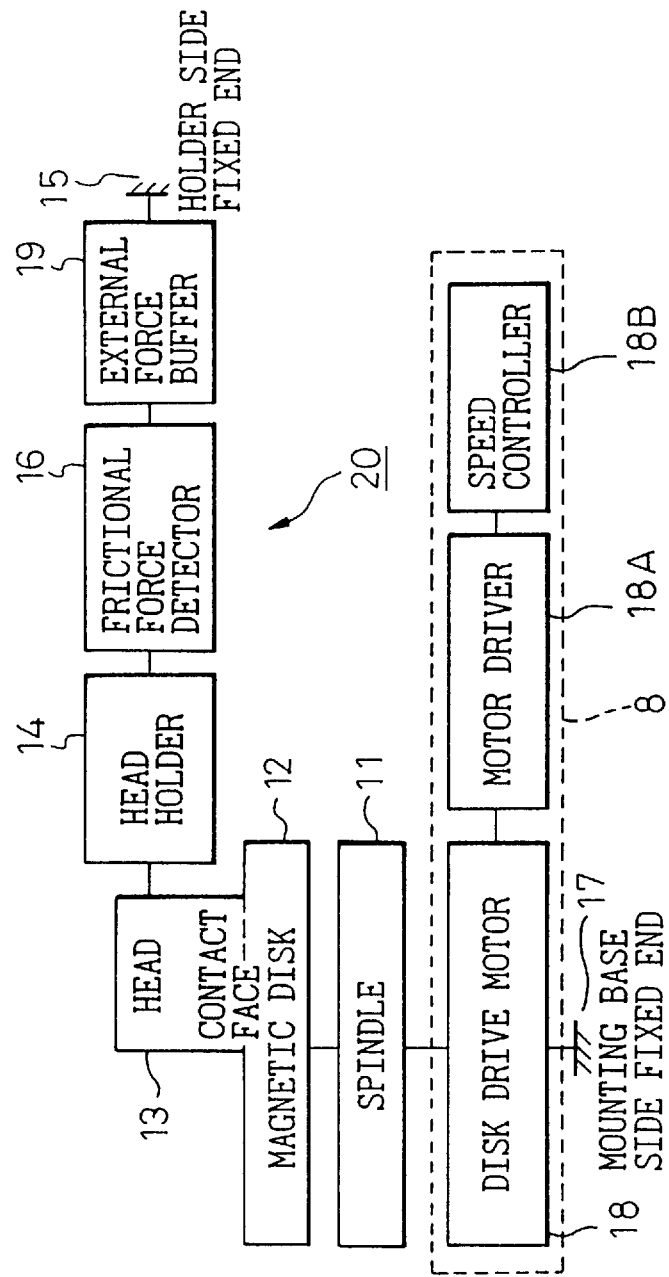
FIG. 8A is a block diagram showing a configuration of a static friction force measuring apparatus according to a second embodiment of the invention.

FIG. 8A is a block diagram showing a configuration of a static friction force measuring apparatus 20 according to a second embodiment of the invention for measuring the static friction force between the magnetic disk 12 and the head 13. In FIG. 8A, those component parts identical to the corresponding ones of the static friction force measuring apparatus 10 of the first embodiment are designated by the same reference numerals, respectively. In the static friction force measuring apparatus 20 according to the second embodiment, the magnetic disk 12 is fixed on the spindle 11 providing a mounting base, and the rotative axis of the spindle 11 is coupled to the rotative axis of a disk drive motor 18. The disk drive motor 18 is secured to the mounting base side fixed end of the apparatus. Further, the disk drive motor 18 is connected to a motor driver 18A and a speed controller 18B.

The head 13, on the other hand, has the air-bearing surface thereof in contact with the upper surface of the magnetic disk 12 thereby constituting a contact surface. The head 13 is held by a head holder 14, which in turn is in contact with a frictional force detector 16. An external force buffer 19 is interposed between the frictional force detector 16 and the holder-side fixed end 15 of the apparatus.

Figure 8B:
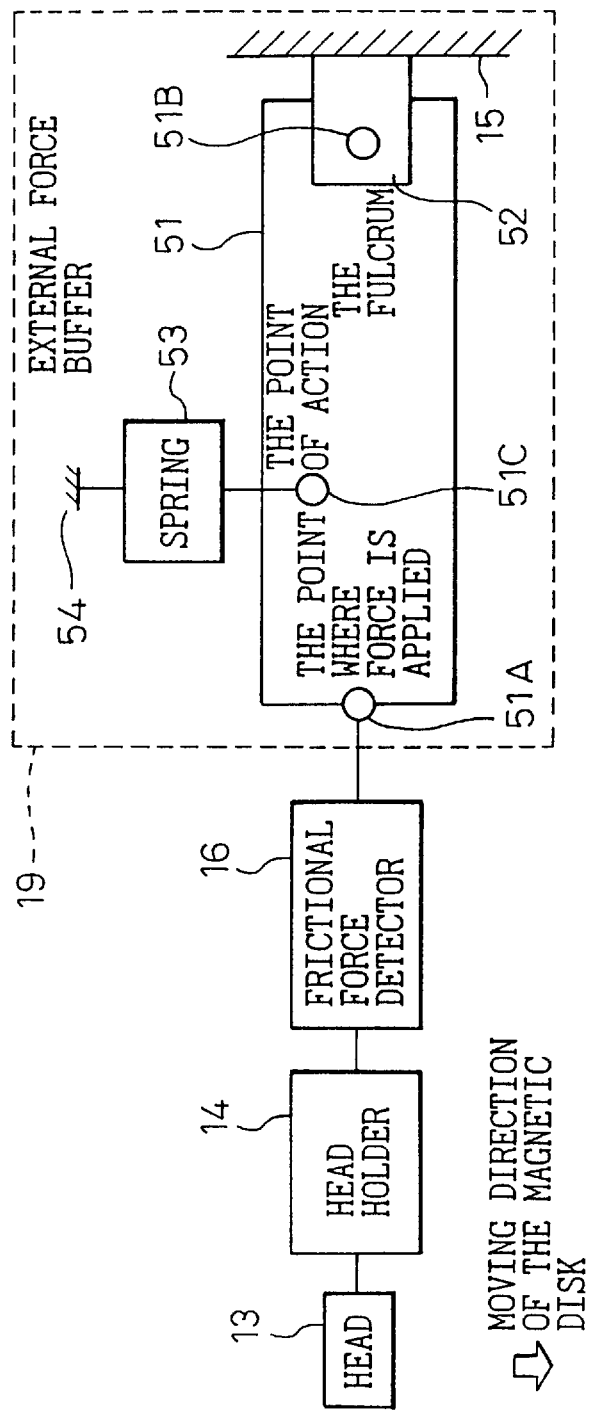
FIG. 8B is a diagram showing a specific example configuration of a part of the static friction force measuring apparatus of FIG. 8A.

FIG. 8B shows more specifically a configuration of the component parts from the head 13 to the holder-side fixed end 15 of the static friction force measuring apparatus 20 of FIG. 8A. The external force buffer 19 according to this embodiment includes a rod 51, a bracket 52 for swingably holding the rod 51 at the first holder-side fixed end 15, and a spring 53 for supporting a predetermined portion of the rod 51 at the second holder-side fixed end 54. A longitudinal end 51A of the rod 51 of the external force buffer 19 is mounted on the frictional force detector 16, and the other end 51B of the rod 51 is mounted on the first holder-side fixed end 15 through the bracket 52. An end of the spring 53 is mounted at a point 51C between a point where the rod 51 is connected with the frictional force detector 16 and a point where the rod 51 is mounted on the bracket 52. The other end of the spring 53 is supported at the second holder-side fixed end 54.

In the external force buffer 19 configured as described above, the point 51A where the rod 51 is mounted on the frictional force detector 16 functions as a point where force is applied or point of application, the point 51B where the rod 51 is mounted on the bracket 52 functions as a fulcrum, and the point 51C where the spring 53 is mounted on the rod 51 acts as a point of action. According to this embodiment, the external force exerted along the direction in which the medium is conveyed is balanced by the elastic force of the spring 53.

Figure 8C:
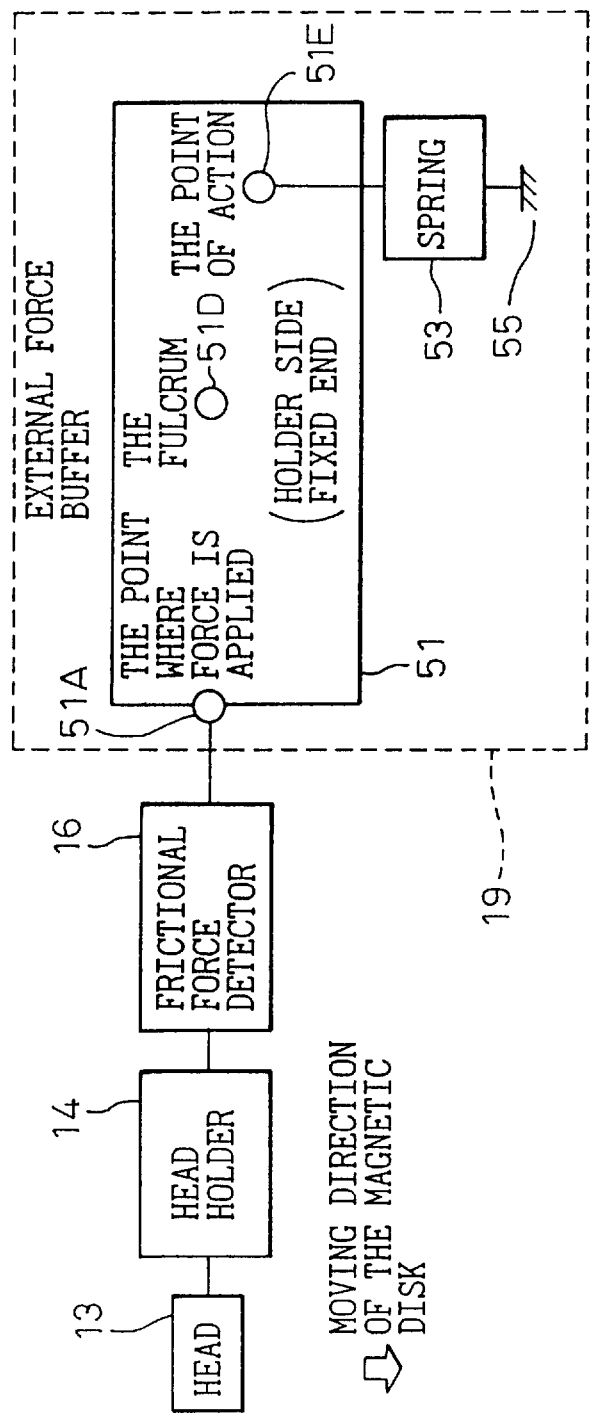
FIG. 8C is a diagram showing another specific example configuration of a part of the static friction force measuring apparatus of FIG. 8A.

FIG. 8C more specifically shows a configuration of the component parts from the head 13 to the holder-side fixed end 15 of the static friction force measuring apparatus 20 in FIG. 8A, in which a configuration of the external buffer 19 according to another embodiment is shown in detail. The external buffer 19 according to this embodiment includes a rod 51 and a spring 53. A longitudinal end 51A of the rod 51 is mounted on the frictional force detector 16, and a central portion 51D along the length of the rod 51 is mounted rotatably on the holder-side fixed end 15 through a pin 51D. Also, an end of the spring 53 is mounted at a predetermined portion 5E at the other end of the rod 51. The other end of the spring 53 is supported on the second holder-side fixed end 55.

In the external force buffer 19 configured as mentioned above, the point 1A where the rod 51 is mounted on the frictional force detector 16 functions as a point of application, the central point 51D of the rod 51 functions as a fulcrum, and the point 51E where the rod 51 is mounted on the spring 53 functions as a point of action. According to this embodiment, as in the above-mentioned embodiment, the external force exerted along the direction of medium movement is balanced by the elastic force of the spring 53.

In the external buffer 19 shown in FIGS. 8B and 8C, the friction force is determined by the product of the spring pressure of the head 13 and the friction coefficient of the head-disk contact surface. Upon application of an external force thereto, therefore, the head 13 and the disk 12 move integrally and the spring 53 of the external force buffer 19 extends thereby to suppress the change of the relative positions of head and disk. In the case where the restitutive force of the spring 53 exceeds the maximum static friction force between head and disk, the relative positions of the head 13 and the disk 12 undergo a change.

Figure 9A:
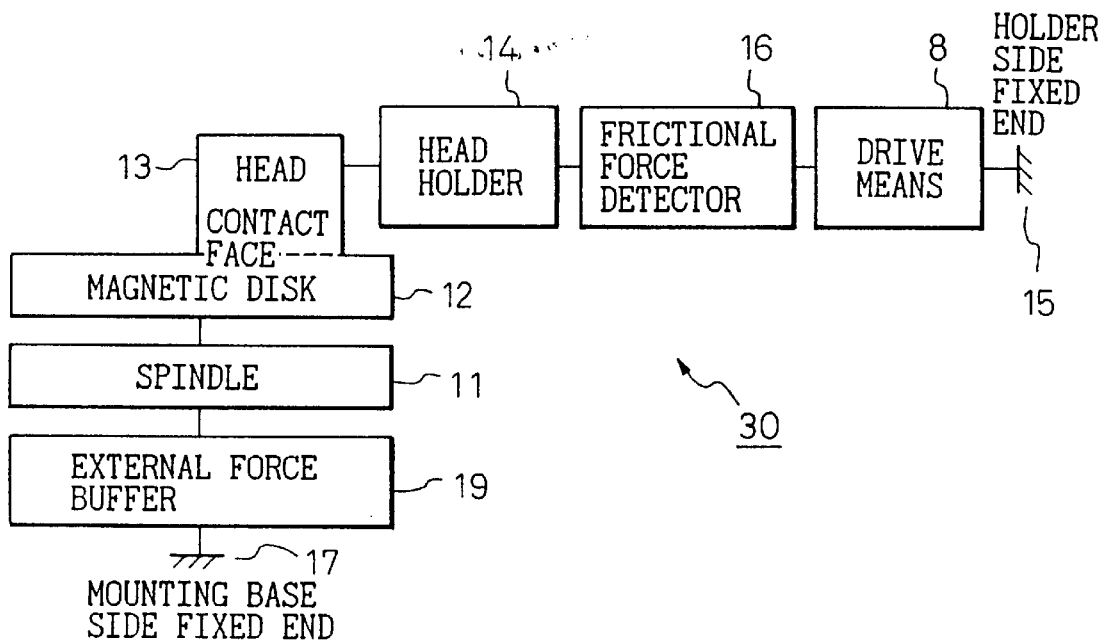
FIG. 9A is a block diagram showing a configuration of a static friction force measuring apparatus according to a third embodiment of the invention.

FIG. 9A is a block diagram showing a configuration of a static friction force measuring apparatus 30 according to a third embodiment of the invention for measuring the static friction force between the magnetic disk 12 and the head 13. In FIG. 9A, those component parts identical to the corresponding parts of the static friction force measuring apparatus 10 according to the first embodiment are designated by the same reference numerals, respectively. With the static friction force measuring apparatus 30 according to the third embodiment, the magnetic disk 12 is fixed on a spindle 11 providing a mounting base, the rotative axis of the spindle 11 is connected to an end of an external force buffer 19, and the other end of the external force buffer 19 is secured to the mounting base side fixed end 17 of the apparatus.

The head 13 has the air-bearing surface thereof in contact with the upper surface of the magnetic disk 12 thereby constituting a contact surface. The head 13 is held by a head holder 14, which in turn is connected to a frictional force detector 16. A drive means 18 is interposed between the frictional force detector 16 and a holder-side fixed end 15 of the apparatus.

Figure 9B:
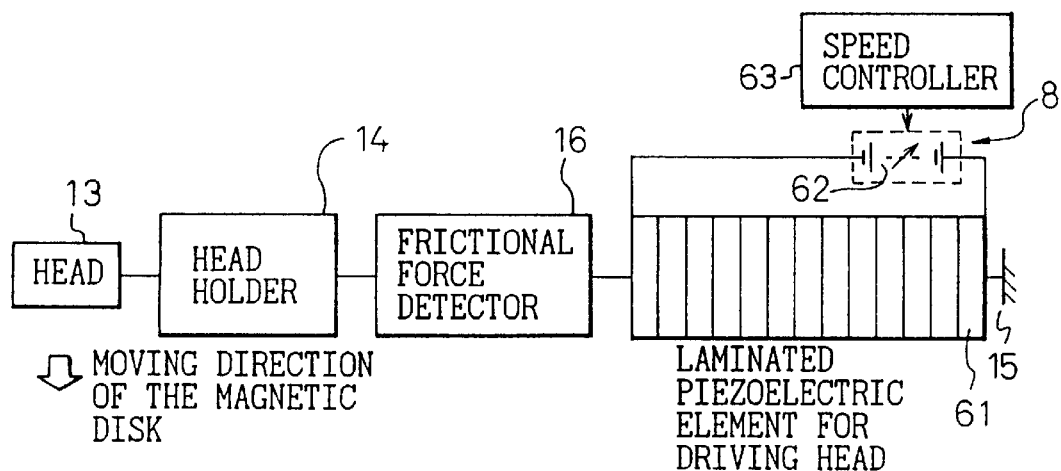
FIG. 9B is a diagram showing a specific example configuration of a part of the static friction force measuring apparatus of FIG. 9A.

FIG. 9B specifically shows a configuration of the component parts of the static friction force measuring apparatus 30 from the head 13 to the holder-side fixed end 15 in FIG. 9A and a detailed configuration of the drive means 8 according to an embodiment. The drive means 8 according to this embodiment includes a laminated piezoelectric element 61 for driving the head, a variable voltage source 62 for applying a voltage to the laminated piezoelectric element 61 and a speed controller 63 for controlling the output voltage applied from the variable voltage source 62 to the laminated piezoelectric element 61. A longitudinal end of the laminated piezoelectric element 61 is connected to the frictional force detector 16, and the other end thereof to the holder-side fixed end 15. The variable voltage source 62 applies to the laminated piezoelectric element 61 a voltage gradually increasing or decreasing in accordance with the control signal generated by the speed controller 63. Upon application of a voltage thereto, the laminated piezoelectric element 61 extends or contracts thereby applying an external force to the head 13.

The laminated piezoelectric element 61 is fabricated of powder, containing lead zirconate titanate as a main component, by adding to it a binder such as PVB (polyvinyl butyral), EC (ethyl cellulose) or MC (methyl cellulose) and a solvent such as acetone or ethyl alcohol, and the resulting substance in slurry form is formed into a green sheet 200 $\mu$m thick by a doctor blade process. Then, an internal electrode is printed on the green sheet using Pt, Ag-Pd or the like as a material by screen printer in accordance with an internal electrode pattern. A plurality of green sheets are formed in about 50 layers with the internal electrodes alternately interposed therein and baked at about 1300° C. thereby to complete the laminated piezoelectric element 61.

As described above, in the static friction force measuring apparatus 30 according to the third embodiment, an external force is exerted by driving the head 13 using the laminated piezoelectric element 61. In this case, the external force buffer 19 is preferably configured substantially as a parallelopipedal or spiral elastic member.

Figure 9C:
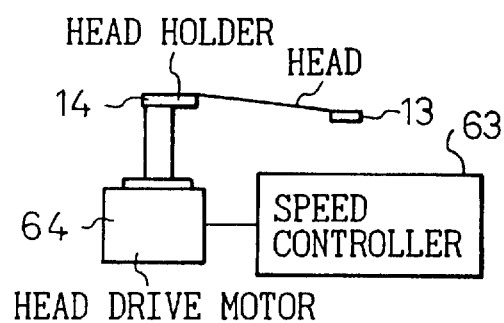
FIG. 9C is a diagram showing a modification of the configuration of the apparatus of FIG. 9B.

As a modification of the head drive means 8 shown in FIG. 9B, the head drive motor 64 shown in FIG. 9C may be used with equal effect. In this case, the external force buffer 19 is preferably configured as a torsion spring.

Further, as a second modification of FIG. 9B, the spindle 11 is connected to a high-speed motor 65 drivable at such a rotational speed as to cause the head to fly, which high-speed motor 65 may be electrically locked when measuring the friction force.

FIG. 10A is a block diagram showing a configuration of a static friction force measuring apparatus 40 according to a fourth embodiment of the invention for measuring the static friction force between the magnetic disk 12 and the head 13. In FIG. 10A, those component parts identical to the corresponding parts of the static friction force measuring apparatus 10 according to the first embodiment are designated by the same reference numerals, respectively. In the static friction force measuring apparatus 40 according to the fourth embodiment, the magnetic disk 12 is fixed on a spindle 11 providing a mounting base, and the other end of the spindle 11 is secured to the mounting base side fixed end 17 of the apparatus.

The head 13, on the other hand, has the contact surface thereof in contact with the upper surface of the magnetic disk 12. The head 13 is held by a head holder 14, which in turn is connected to a frictional force detector 16. An external force buffer 19 and a drive means 8 are arranged in that order between the frictional force detector 16 and a holder-side fixed end 15 of the apparatus.

Figure 10B:
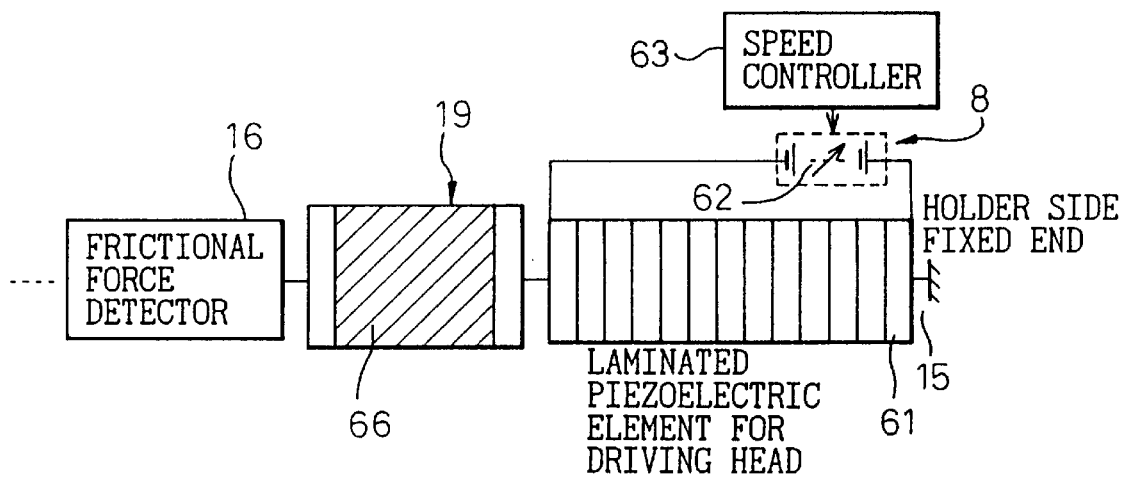
FIG. 10B is a diagram showing a specific example configuration of a part of the static friction force measuring apparatus shown in FIG. 10A.

FIG. 10B specifically shows a configuration of the component parts of the static friction force measuring apparatus 40 of FIG. 10A from the head 13 to the holder-side fixed end 15 including a detailed configuration of the drive means 8 and the external force buffer 19 according to an embodiment.

The drive means 8 according to this embodiment includes a laminated piezoelectric element 61 for driving the head, a variable voltage source 62 for applying a voltage to the laminated piezoelectric element 61, and a speed controller 63 for controlling the output voltage applied from the variable voltage source 62 to the laminated piezoelectric element 61. A longitudinal end of the laminated piezoelectric element 61 is connected to the external force detector 19, and the other end thereof connected to the holder-side fixed end 15. The variable voltage source 62 applies to the laminated piezoelectric element 61 a voltage which is gradually increasing or decreasing in accordance with the control signal generated by the speed controller 63. The laminated piezoelectric element 61 supplied with this voltage extends or contracts thereby to apply an external force to the head 13.

The external force buffer 19 is preferably a substantially parallelopipedal or spiral elastic member 66.

Figure 9D:
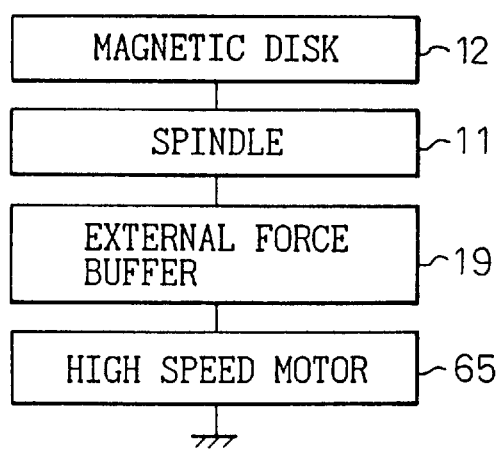
FIG. 9D is a diagram showing a modification of the configuration of a part of the apparatus shown in FIG. 9A.
Figure 10C:
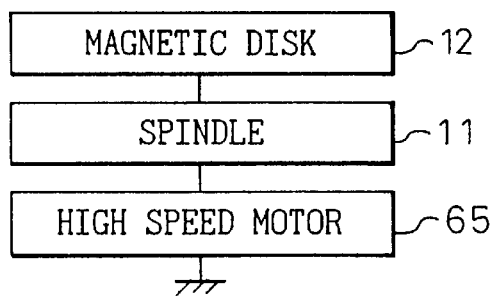
FIG. 10C is a diagram showing a modification of the configuration of a part of the apparatus shown in FIG. 10A.

A modification of the head drive means 8 may be configured as shown in FIG. 9C. In this case, the external force buffer is preferably a torsion spring. Also, a second modification may have a similar configuration to FIG. 9D in which, as shown in FIG. 10C, the spindle 11 is connected to a high-speed motor 65 drivable at such a rotational speed as to cause the head to fly, which high-speed motor 65 may be electrically locked at the time of measuring the friction force.

Figure 11A:
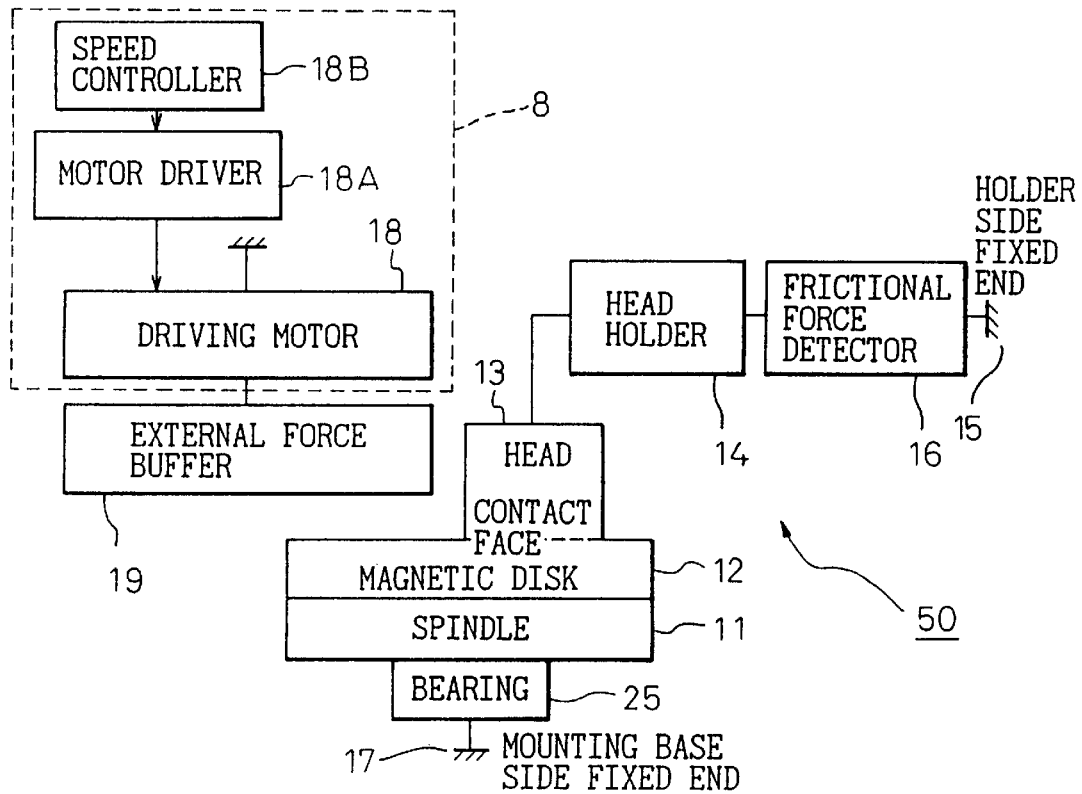
FIG. 11A is a block diagram showing a configuration of a static friction force measuring apparatus according to a fifth embodiment of the invention.

FIG. 11A is a block diagram showing a configuration of a static friction force measuring apparatus 50 according to a fifth embodiment of the invention for measuring the static friction force between the magnetic disk 12 and the head 13. In FIG. 11A, those component parts identical to the corresponding parts of the static friction force measuring apparatus 10 according to the first embodiment are designated by the same reference numerals, respectively. In the static friction force measuring apparatus 50 according to the fifth embodiment, the magnetic disk 12 is fixed on a spindle 11 providing a mounting base, and the other end of the spindle 11 is secured to the mounting base side fixed end 17 of the apparatus through a bearing 25.

The head 13 has the air-bearing surface thereof in contact with the upper surface of the magnetic disk 12 thereby constituting a contact surface. The head 13 is held by the head holder 14, which in turn is connected to the frictional force detector 16. The other end of the frictional force detector 16 is fixedly connected to the holder-side fixed end 15.

Further, according to the fifth embodiment, the magnetic disk drive motor 18 is arranged above the magnetic disk 12 and out of contact with it, and the external force buffer 19 is interposed between the drive motor 18 and the magnetic disk 12. Also, the disk drive motor 18 is connected with a motor driver 18A and a speed controller 18B. For the disk drive motor 18 and the spindle 11 to be arranged out of contact with each other so that the spindle 11 is driven by the disk drive motor 18, a magnet is arranged at least on one of the disk drive motor 18 and the spindle 11. In this case, the rotation of the disk drive motor 18 subjects the spindle 11 to the operation of the external force buffer 19 due to the attractive force, repulsive force or inductive force between the magnets.

Figure 11B:
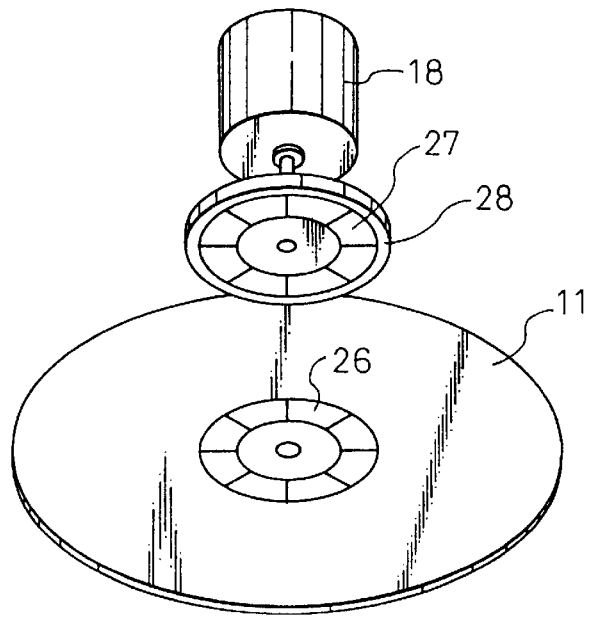
FIG. 11B is a diagram showing a specific example configuration of a part of the static friction force measuring apparatus shown in FIG. 11A.

FIG. 11B specifically shows a configuration of the disk drive motor 18 and the spindle 11 included in the static friction force measuring apparatus 50 of FIG. 11A according to an embodiment. In this embodiment, a drive plate 28 is mounted on the rotational axis of the disk drive motor 18 and has a plurality of concentric magnets 27 embedded in the rotational axis thereof. The magnets 27 are arranged in alternate polarities. The spindle 11, on the other hand, has a plurality of magnets 26 similar to the magnets 27 embedded concentrically in the rotational axis of the spindle 11 at positions in opposed relation to the drive plate 28.

As a result, with the rotation of the disk drive motor 18, the spindle 11 is driven to rotate out of contact with the disk drive motor 18 under the attractive force between the magnets. In the case where the magnets 26 are not provided on the spindle 11, the portion of the spindle 11 opposed to the drive plate 28 is formed of a magnetic material such as iron.

In the present embodiment, the external force buffer 19 and the disk drive motor 18 may be arranged under instead of above the magnetic disk 13. In such a case, the magnetic material or the magnets on the spindle 11 are in opposed relation to the external force buffer 19 through a central hole of the magnetic disk 12.

In the case of the static friction force measuring apparatus 50 according to the fifth embodiment, the magnetic attractive force or magnetic repulsive force between the spindle 11 and the disk drive motor 18 absorbs the external force. The relative positions of the magnetic head 13 and the magnetic disk 12, therefore, are not displaced.

In the configuration of the above-mentioned embodiments, the magnetic disk 12 and the head 13 are stacked on the spindle 11. As an alternative, the medium may be arranged in vertical position while the medium mounting base and other component parts are arranged horizontally with equal effect.

FIG. 12 is a table showing the result of measurement of the static friction coefficient between the magnetic disk 12 and the magnetic head 13 by the static friction force measuring apparatus 10 according to the invention, as compared with the true value of the static friction coefficient, the result of measurement of the static friction coefficient by the conventional static friction force measuring apparatus using a $\mu$ sensor and the result of measurement of the static friction coefficient by the conventional static friction force measuring apparatus using a load cell. A false low acceleration motor described with reference to FIG. 7 is used as the drive means for the static friction force measuring apparatus 10 according to the invention.

The true value of the static friction coefficient between the magnetic head 13 and the magnetic disk 12 is the one obtained when the magnetic disk 12 is driven manually. A magnetic recording and reproduction apparatus two generations old which is low in magnetic recording density is used as sample A, a magnetic recording and reproduction apparatus which is produced one generation ago higher in magnetic recording density is used as sample B, and the latest magnetic recording and reproduction apparatus still higher in magnetic recording density is used as sample C.

As seen from the table, the static friction force measuring apparatus 10 according to the invention can produce a static friction force substantially near to the true value thereof for all samples A, B and C. With the conventional static friction force measuring apparatus using a load cell, by contrast, the static friction force is detected as a value lower than the true value due to the response delay as described with reference to FIG. 2A. In the conventional static friction force measuring apparatus using a $\mu$ sensor, on the other hand, it can be seen that the static friction force is undesirably detected as a value larger than the true value due to the resonance described with reference to FIG. 2B.

As described above in detail with reference to the embodiments, according to the present invention, even when an external force is exerted to such an extent as to displace the relative positions of the magnetic head and the magnetic recording medium by the drive means, the relative positions of the head and the magnetic disk (medium) are kept unchanged by the external force buffer until the maximum friction force is exceeded, thereby making it possible to accurately measure the maximum static friction force.

What is claimed is:

1. A static friction force measuring apparatus for measuring the static friction characteristic between a first object and a second object in contact with the first object, comprising:

a mounting base having said first object fixed at an end thereof and the other end thereof secured to a first fixed end of said apparatus;

a holder having an end thereof holding said second object and the other end thereof secured to a second fixed end of the apparatus;

a frictional force detector, arranged at an arbitrary position between said holder-side fixed end and said mounting base side fixed end other than the portion where said first end and second objects are in contact with each other, for measuring a maximum static friction force immediately before the displacement begins between said two objects;

drive means for applying an external force to a selected one of (a) between said holder and said holder-side fixed end and (b) between said mounting base and said mounting base side fixed end of the apparatus in a direction substantially parallel with the contact surface between said two objects;

an external force buffer for suppressing the displacement between the relative positions of said two objects to the extent that the external force, exerted substantially in parallel with the contact surface of the two objects, exceeds the maximum static friction force, said buffer being arranged between said mounting base and said mounting base side fixed end of the apparatus; and a speed controller mounted on said drive means for controlling the relative speeds of said holder and said mounting base to a level sufficiently low as compared with the resonance frequency of said frictional force detector.

2. A static friction force measuring apparatus according to claim 1, wherein:

said first object is a magnetic disk, said second object is a magnetic head, said mounting base is a spindle carrying said magnetic disk, said drive means is a motor having a rotative axis coaxial with the rotational axis of said spindle, and said elastic member is directly coupled between the rotative axis of said spindle and the rotative axis of said motor.

3. A static friction force measuring apparatus according to claim 1, wherein:

said first object is a magnetic disk, said second object is a magnetic head, said mounting base is a spindle carrying said magnetic disk, said drive means includes a motor having a rotative axis not coaxial with the rotational axis of said spindle and a roller mounted on the rotative axis of said motor and having an outer peripheral portion thereof frictionally engaging an outer peripheral portion of said spindle, and said elastic member is directly coupled between the rotative axis of said roller and the rotative axis of said motor.

4. A static friction force measuring apparatus according to claim 1, wherein:

said first object is a magnetic disk, said second object is a magnetic head, said mounting base is a spindle carrying the magnetic disk, said drive means is a motor having the rotational axis thereof coaxial with the rotative axis of said spindle, and said external force buffer includes a rod and a spring, said rod having a fulcrum at the holder-side fixed end, a point of application at the the point where said rod is connected with said friction force detector and a point of action between said fulcrum and said point of application, said spring having an end thereof mounted on said point of action of said rod and the other end thereof secured to a portion other than said holder-side fixed end.

5. A static friction force measuring apparatus according to claim 1, wherein:

said first object is a magnetic disk, said second object is a magnetic head, said mounting base is a spindle carrying said magnetic disk, said drive means is a motor having a rotative axis thereof coaxial with the rotative axis of said spindle, and said external force buffer includes a rod and a spring, said rod having a fulcrum at the holder-side fixed end, a point of application at the point where said rod is connected with said friction force detector and a point of action on the side opposite to the point of application with respect to said fulcrum, said spring having an end thereof mounted on said point of action of said rod and the other end thereof fixed at a position other than said holder-side fixed end of the apparatus.

6. A static friction force measuring apparatus according to claim 1, wherein:

said first object is a magnetic disk, said second object is a magnetic head, said mounting base is a spindle carrying said magnetic disk, said drive means is a piezoelectric device interposed between said frictional force detector and said holder-side fixed end, and said elastic member is directly coupled between the rotative axis of said spindle and said mounting base side fixed end of the apparatus.

7. A static friction force measuring apparatus according to claim 1, wherein:

said first object is a magnetic disk, said second object is a magnetic head, said mounting base is a spindle carrying said magnetic disk, said drive means is a piezoelectric device interposed between said frictional force detector and said holder-side fixed end, and said external force buffer includes a roller having a rotative axis not coaxial with the rotative axis of said spindle and said elastic member directly coupled between the rotative axis of said roller and the mounting side fixed end of the apparatus.

8. A static friction force measuring apparatus according to claim 1, wherein:

said first object is a magnetic disk, said second object is a magnetic head, said external force buffer is arranged between said holder-side fixed end and said holder, and said drive means includes an external force buffer made of said elastic member and a piezoelectric device arranged at said holder-side fixed end.

9. A static friction force measuring apparatus according to claim 1, wherein:

said first object is a magnetic disk, said second object is a magnetic head, said mounting base is a spindle having a bearing, said frictional force detector is arranged between said holder and said holder side fixed end, and said drive means is arranged above or under said mounting base in a spaced apart and opposed relationship therewith, a magnet is arranged on at least one of said mounting base and said drive means, the other of said mounting base and said drive means has a magnet arranged thereon or formed of a magnetic material, and said external force buffer is means for generating a selected one of a magnetic attractive force and a magnetic repulsive force between said drive means and said mounting base.

10. A static friction force measuring apparatus for measuring the static friction characteristic between a first object and a second object in contact with the first object, comprising:

a mounting base having said first object fixed at an end thereof and the other end thereof secured to a first fixed end of said apparatus;

a holder having an end thereof holding said second object and the other end thereof secured to a second fixed end of the apparatus;

a frictional force detector arranged at an arbitrary position between said holder-side fixed end and said mounting base side fixed end other than the portion where said first end and second objects are in contact with each other for measuring a maximum static friction force immediately before the displacement begins between said two objects;

drive means for applying an external force to a selected one of (a) between said holder and said holder-side fixed end and (b) between said mounting base and said mounting base side fixed end of the apparatus in a direction substantially parallel with the contact surface between said two objects;

an external force buffer including suppressing the displacement between the relative positions of said two objects to the extent that the external force, exerted substantially in parallel with the contact surface of the two objects, exceeds the maximum static friction force, said external force buffer being arranged between said holder-side fixed end and said holder; and a speed controller mounted on said drive means for controlling the relative speeds of said holder and said mounting base to a level sufficiently low as compared with the resonance frequency of said frictional force detector.

11. A static friction force measuring apparatus according to claim 1, wherein said external force buffer is an elastic member taking a shape of one of a rectangular parallel-piped and a spiral.

12. A static friction force measuring apparatus according to claim 10, wherein said external force buffer is an elastic member taking a shape of one of a rectangular parallel-piped and a spiral.

* * * * *

UNITED STATES PATENT AND TRADEMARK OFFICE
CERTIFICATE OF CORRECTION

PATENT NO. : 5,859,357
DATED : January 12, 1999
INVENTOR(S) : Kameyama et al.

It is certified that error appears in the above-identified patent and that said Letters Patent is hereby corrected as shown below:

Column 1, line 52, delete "friction is" and insert --friction $\mu s$-- therfor

Column 7, line 17, delete "(i" and insert --($\mu$-- therefor

Column 13, line 47, delete "result" and insert --results-- therefor

Column 13, line 47, after "of" insert --the--

Column 13, line 47, delete "measurement" and insert --measurements-- therefor

Column 15, line 15, delete "claim 1" and insert --claim 10-- therefor

UNITED STATES PATENT AND TRADEMARK OFFICE
CERTIFICATE OF CORRECTION

PATENT NO. : 5,859,357
DATED : January 12, 1999
INVENTOR(S) : Kameyama et al.

It is certified that error appears in the above-identified patent and that said Letters Patent is hereby corrected as shown below:

Column 15, line 30, delete "claim 1" and insert --claim 10-- therefor

Column 16, line 2, delete "claim 1"and insert --claim 10-- therefor

Signed and Sealed this

Fourteenth Day of December, 1999

Attest:

Q. TODD DICKINSON

Attesting Officer

Acting Commissioner of Patents and Trademarks